United States Patent
Sieger et al.

(10) Patent No.: US 6,608,055 B2
(45) Date of Patent: Aug. 19, 2003

(54) CRYSTALLINE ANTICHOLINERGIC, PROCESSES FOR PREPARING IT AND ITS USE FOR PREPARING A PHARMACEUTICAL COMPOSITION

(75) Inventors: Peter Sieger, Mittelbiberach (DE); Ulrike Werthmann, Mittlebiberach (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/167,198

(22) Filed: Jun. 11, 2002

(65) Prior Publication Data

US 2003/0087927 A1 May 8, 2003

Related U.S. Application Data

(60) Provisional application No. 60/313,519, filed on Aug. 20, 2001.

(30) Foreign Application Priority Data

Jun. 22, 2001 (DE) .......................... 101 29 710
Apr. 8, 2002 (DE) .......................... 102 15 436

(51) Int. Cl.$^7$ .................. A61K 31/537; C07D 498/18
(52) U.S. Cl. ................. 514/229.8; 544/101; 544/99; 544/291; 514/229.5; 514/230.5; 546/89
(58) Field of Search ............... 514/230.5, 229.5, 514/291, 229.8; 544/99, 101; 546/89

(56) References Cited

U.S. PATENT DOCUMENTS

| | | |
|---|---|---|
| 5,610,163 A | 3/1997 | Banholzer et al. |
| 9,961,822 | 9/2001 | Banholder et al. |

FOREIGN PATENT DOCUMENTS

| | | |
|---|---|---|
| EP | 0 418 716 A1 | 3/1991 |
| WO | WO 02/30928 A | 4/2002 |
| WO | WO 02/051840 A | 7/2002 |

OTHER PUBLICATIONS

Barnes, P.J. et al. : Tiotropium bromide, a novel lon–acting muscarinic antagonist for the treatment of obstructive airway disease. Life Sci. vol. 56, pp. 853–859, 1995.*

* cited by examiner

*Primary Examiner*—Charanjit S Aulakh
(74) *Attorney, Agent, or Firm*—Robert P. Raymond; Mary-Ellen M. Devlin; Alan R. Stempel

(57) ABSTRACT

The invention relates to crystalline anhydrous (1α,2β,4β, 5α,7β)-7-[(hydroxydi-2-thienylacetyl)oxy]-9,9-dimethyl-3-oxa-9-azoniatricyclo[3.3.1.0$^{2,4}$]nonane-bromide, processes for preparing it and its use for preparing a pharmaceutical composition, particularly for preparing a pharmaceutical composition with an anticholinergic activity.

18 Claims, No Drawings

CRYSTALLINE ANTICHOLINERGIC, PROCESSES FOR PREPARING IT AND ITS USE FOR PREPARING A PHARMACEUTICAL COMPOSITION

The invention relates to a crystalline (1α,2β,4β,5α,7β)-7-[(hydroxydi-2-thienylacetyl)oxy]-9,9-dimethyl-3-oxa-9-azoniatricyclo[3.3.1.0$^{2,4}$]nonane-bromide in anhydrous form, processes for preparing it and its use for preparing a pharmaceutical composition, particularly for preparing a pharmaceutical composition with an anticholinergic activity.

BACKGROUND OF THE INVENTION

The compound (1α,2β,4β,5α,7β)-7-[(hydroxydi-2-thienylacetyl)oxy]-9,9-dimethyl-3-oxa-9-azoniatricyclo[3.3.1.0$^{2,4}$]nonane-bromide, is known from European Patent Application EP 418 716 A1 and has the following chemical structure:

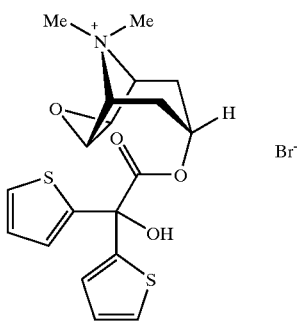

(I)

The compound has valuable pharmacological properties and is known by the name tiotropium bromide (BA679BR). Tiotropium bromide is a highly effective anticholinergic and can therefore provide therapeutic benefit in the treatment of asthma or COPD (chronic obstructive pulmonary disease).

Tiotropium bromide is preferably administered by inhalation. Suitable inhalable powders packed into appropriate capsules (inhalettes) and administered by suitable powder inhalers may be used. Alternatively, it may be administered by the use of suitable inhalable aerosols. These also include powdered inhalable aerosols which contain, for example, HFA134a, HFA227 or mixtures thereof as propellant gas.

The correct manufacture of the abovementioned compositions which are suitable for use for the administration of a pharmaceutically active substance by inhalation is based on various parameters which are connected with the nature of the active substance itself. In pharmaceutical compositions which are used like tiotropium bromide in the form of inhalable powders or inhalable aerosols, the crystalline active substance is used in ground (micronised) form for preparing the formulation. Since the pharmaceutical quality of a pharmaceutical formulation requires that the active substance should always have the same crystalline modification, the stability and properties of the crystalline active substance are subject to stringent requirements from this point of view as well. It is particularly desirable that the active substance should be prepared in the form of a uniform and clearly defined crystalline modification. It is also particularly desirable that the active substance be prepared in a crystalline form which does not tend to form polymorphs.

Apart from the requirements indicated above, it should be generally borne in mind that any change to the solid state of a pharmaceutical composition which is capable of improving its physical and chemical stability gives a significant advantage over less stable forms of the same medicament.

The aim of the invention is thus to provide a new, stable crystalline form of the compound tiotropium bromide which meets the stringent requirements imposed on pharmaceutically active substances as mentioned above.

DETAILED DESCRIPTION OF THE INVENTION

It has been found that, depending on the choice of conditions which can be used when purifying the crude product obtained after industrial manufacture, tiotropium bromide occurs in various crystalline modifications.

It has been found that these different modifications can be deliberately produced by selecting the solvents used for the crystallisation as well as by a suitable choice of the process conditions used in the crystallisation process.

Surprisingly, it has been found that, starting from the monohydrate of tiotropium bromide, which can be obtained in crystalline form by choosing specific reaction conditions, it is possible to obtain an anhydrous crystalline modification of tiotropium bromide which meets the stringent requirements mentioned above and thus solves the problem on which the present invention is based. Accordingly the present invention relates to this crystalline anhydrous tiotropium bromide. Any reference to tiotropium bromide anhydrate within the scope of the present invention is to be regarded as a reference to the crystalline tiotropium bromide according to the invention in anhydrous form.

According to another aspect, the present invention relates to a process for preparing the crystalline form of anhydrous tiotropium bromide. This preparation process is characterised in that tiotropium bromide, which has been obtained for example by the method disclosed in EP 418 716 A1, is taken up in water, the mixture obtained is heated and finally the hydrate of tiotropium bromide is crystallised while cooling slowly. Anhydrous crystalline tiotropium bromide can then be obtained from the resulting crystalline tiotropium bromide monohydrate by drying.

The present invention further relates to crystalline anhydrous tiotropium bromide which may be obtained by the above method.

One aspect of the present invention relates to a process for preparing crystalline anhydrous tiotropium bromide starting from crystalline tiotropium bromide monohydrate which is described in more detail hereinafter.

In order to prepare the crystalline monohydrate, tiotropium bromide, which has been obtained for example according to the method disclosed in EP 418 716 A1, has to be taken up in water and heated, then purified with activated charcoal and, after removal of the activated charcoal, the tiotropium bromide monohydrate has to be crystallised out slowly while cooling gently. The anhydrous form is obtained from these crystals by careful heating to more than 50° C., preferably 60–100° C., more particularly to 70–100° C. under reduced pressure, preferably under a high vacuum, over a period of from 15 minutes to 24 hours, preferably 20 minutes to 12 hours.

The method described below is preferably used according to the invention. In a suitably dimensioned reaction vessel the solvent is mixed with tiotropium bromide, which has been obtained for example according to the method disclosed in EP 418 716 A1. 0.4 to 1.5 kg, preferably 0.6 to 1 kg, most preferably about 0.8 kg of water are used as solvent per mole of tiotropium bromide used. The mixture obtained is heated with stirring, preferably to more than 50° C., most preferably to more than 60° C. The maximum temperature which can be selected will be determined by the boiling point of the solvent used, i.e. water. Preferably the mixture is heated to a range from 80–90° C. Activated charcoal, dry or moistened with water, is added to this solution. 10 to 50 g, more preferably 15 to 35 g, most preferably about 25 g of activated charcoal are put in per mole of tiotropium bromide used. If desired, the activated charcoal is suspended in water before being added to the solution containing the tiotropium bromide. 70 to 200 g, preferably 100 to 160 g, most preferably about 135 g water are used to suspend the activated charcoal, per mole of tiotropium bromide used. If the activated charcoal is suspended in water prior to being added to the solution containing the tiotropium bromide, it is advisable to rinse with the same amount of water.

After the activated charcoal has been added, stirring is continued at constant temperature for between 5 and 60 minutes, preferably between 10 and 30 minutes, most preferably about 15 minutes, and the mixture obtained is filtered to remove the activated charcoal. The filter is then rinsed with water. 140 to 400 g, preferably 200 to 320 g, most preferably about 270 g of water are used for this, per mole of tiotropium bromide used.

The filtrate is then slowly cooled, preferably to a temperature of 20–25° C. The cooling is preferably carried out at a cooling rate of 1 to 10° C. per 10 to 30 minutes, preferably 2 to 8° C. per 10 to 30 minutes, more preferably 3 to 5° C. per 10 to 20 minutes, most preferably 3 to 5° C. roughly per 20 minutes. If desired, the cooling to 20 to 25° C. may be followed by further cooling to below 20° C., most preferably to 10 to 15° C.

Once the filtrate has cooled, it is stirred for between 20 minutes and 3 hours, preferably between 40 minutes and 2 hours, most preferably about one hour, to complete the crystallisation.

The crystals formed are finally isolated by filtering or suction filtering the solvent. If it proves necessary to subject the crystals obtained to another washing step, it is advisable to use water or acetone as the washing solvent. 0.1 to 1.0 l, preferably 0.2 to 0.5 l, most preferably about 0.3 l solvent are used, per mole of tiotropium bromide, to wash the tiotropium bromide monohydrate crystals obtained. If desired the washing step may be repeated.

The product obtained is dried in vacuo or using circulating hot air until a water content of 2.5–4.0% is obtained.

The anhydrous form is obtained from the resulting crystalline tiotropium bromide monohydrate by careful drying at more than 50° C., preferably at 60–100° C., most preferably at 70–100° C., under reduced pressure, preferably in a high vacuum over a period of 15 minutes to 24 hours, preferably 20 minutes to 12 hours, most preferably 30 minutes to 6 hours. The term "reduced pressure" most preferably refers to a pressure of up to $5 \times 10^{-2}$ bar, preferably $1 \times 10^{-2}$ bar, most preferably $5 \times 10^{-3}$ bar.

Most preferably, the abovementioned dehydration to form the anhydrate is carried out at about $1 \times 10^{-3}$ bar or less.

Alternatively to the drying step at elevated temperature under reduced pressure described above, the anhydrous form may also be prepared by storing the crystalline tiotropium bromide monohydrate over a drying agent, preferably over dried silica gel at ambient temperature for a period of 12 to 96 hours, preferably 18 to 72 hours, most preferably at least 24 hours. The anhydrous form thus obtained should be stored more or less dry, depending on the particle size, to preserve its anhydrous state. In the case of coarse crystals of anhydrous tiotropium bromide, which may be prepared for example as described above, storage at <75% r.h. (relative humidity) is sufficient to maintain the anhydrous state. In the micronised state, i.e. where the material has a much larger surface area, water may even be absorbed at lower humidity levels. In order to maintain the anhydrous form in the micronised state, it is therefore advisable to store the anhydrous form of tiotropium bromide over dried silica gel until it is further processed to form the desired inhalable powder containing suitable excipients (e.g. lactose) in addition to tiotropium bromide.

One aspect of the present invention relates to crystalline anhydrous tiotropium bromide which can be obtained using the method described above. The invention further relates to the use of crystalline tiotropium bromide monohydrate for preparing crystalline tiotropium bromide in anhydrous form.

Characterisation of Crystalline Tiotropium Bromide Monohydrate

The tiotropium bromide monohydrate obtainable using the method described above and used as a starting material for preparing the anhydrous crystalline tiotropium bromide according to the invention was investigated by DSC (Differential Scanning Calorimetry). The DSC diagram shows two characteristic signals. The first, relatively broad, endothermic signal between 50–120° C. can be attributed to the dehydration of the tiotropium bromide monohydrate into the anhydrous form. The second, relatively sharp, endothermic peak at 230±5° C. can be put down to the melting of the substance with decomposition. This data was obtained using a Mettler DSC 821 and evaluated using the Mettler STAR software package. The data was recorded at a heating rate of 10 K/min.

Since the substance melts with decomposition (=incongruent melting process), the melting point observed depends to a great extent on the heating rate. At lower heating rates, the melting/decomposition process is observed at significantly lower temperatures, e.g. at 220±5° C. at a heating rate of 3 K/min. It is also possible that the melting peak may be split. The split is all the more apparent the lower the heating rate in the DSC experiment.

The tiotropium bromide monohydrate obtained by the method described above and used as a starting material for preparing the anhydrous crystalline tiotropium bromide according to the invention was characterised by IR spectroscopy. The data was obtained using a Nicolet FTIR spectrometer and evaluated with the Nicolet OMNIC software package, version 3.1. The measurement was carried out with 2.5 µmol of tiotropium bromide monohydrate in 300 mg of KBr. Table 1 shows some of the essential bands of the IR spectrum.

TABLE 1

Attribution of specific bands

| Wave number (cm$^{-1}$) | Attribution | Type of oscillation |
| --- | --- | --- |
| 3570, 3410 | O—H | elongated oscillation |
| 3105 | Aryl C—H | elongated oscillation |
| 1730 | C=O | elongated oscillation |
| 1260 | Epoxide C—O | elongated oscillation |
| 1035 | Ester C—OC | elongated oscillation |
| 720 | Thiophene | cyclic oscillation |

The tiotropium bromide monohydrate obtained by the method described above and used as a starting material for preparing the anhydrous crystalline tiotropium bromide according to the invention was characterised by X-ray structural analysis. The measurements of X-ray diffraction intensity were carried out on an AFC7R-4-circuit diffractometer (Rigaku) using monochromatic copper $K_\alpha$ radiation.

The structural resolution and refinement of the crystal structure were obtained by direct methods (SHELXS86 Program) and FMLQ-refinement (TeXsan Program). Experimental details of the crystalline structure, structural resolution and refinement are collected in Table 2.

TABLE 2

Experimental data on the analysis of the crystalline structure of tiotropium bromide monohydrate.

A. Crystal data

| | |
|---|---|
| Empirical formula | $[C_{19}H_{22}NO_4S_2]$ Br · $H_2O$ |
| Weight of formula | 472.43 + 18.00 |
| colour and shape of crystals | colourless, prismatic |
| dimensions of crystals | 0.2 × 0.3 × 0.3 mm |
| crystal system | monoclinic |
| lattice type | primitive |
| space group | P $2_1$/n |
| lattice constants | a = 18.0774 Å, |
| | b = 11.9711 Å |
| | c = 9.9321 Å |
| | β = 102.691° |
| | V = 2096.96 Å$^3$ |
| formula units per elementary cell | 4 |

B. Measurements of intensity

| | |
|---|---|
| Diffractometer | Rigaku AFC7R |
| X-ray generator | Rigaku RU200 |
| wavelength = | 1.54178 (monochromatic copper $K_\alpha$-radiation) |
| current, voltage | 50 kV, 100 mA |
| take-off angle | 6 |
| crystal assembly | steam-saturated capillary |
| crystal-detector gap | 235 mm |
| detector opening | 3.0 mm vertical and horizontal |
| temperature | 18 |
| determining the lattice constants | 25 reflexes (50.8 <2 <56.2 ) |
| Scan Type | -2 |
| 2 max | 120 |
| measured | 5193 |
| independent reflexes | 3281 ($R_{int}$ = 0.051) |
| corrections | Lorentz polarisation Absorption (Transmission factors 0.56–1.00) crystal decay 10.47% decay |

C. Refinement

| | |
|---|---|
| Reflections (I > 3 I) | 1978 |
| Variable | 254 |
| ratio of reflections/parameters | 7.8 |
| R-values: R, Rw | 0.062, 0.066 |

The X-ray structural analysis carried out showed that crystalline tiotropium bromide monohydrate has a simple monoclinic cell with the following dimensions:
a=18.0774 Å, b=11.9711 Å, c=9.9321 Å, β=102.691°, V=2096.96 Å$^3$.
The atomic coordinates described in Table 3 were determined by the above X-ray structural analysis:

TABLE 3

| | Coordinates | | | |
|---|---|---|---|---|
| Atom | x | y | z | u (eq) |
| Br(1) | 0.63938(7) | 0.0490(1) | 0.2651(1) | 0.0696(4) |
| S(1) | 0.2807(2) | 0.8774(3) | 0.1219(3) | 0.086(1) |
| S(2) | 0.4555(3) | 0.6370(4) | 0.4214(5) | 0.141(2) |
| O(1) | 0.2185(4) | 0.7372(6) | 0.4365(8) | 0.079(3) |
| O(2) | 0.3162(4) | 0.6363(8) | 0.5349(9) | 0.106(3) |
| O(3) | 0.3188(4) | 0.9012(5) | 0.4097(6) | 0.058(2) |
| O(4) | 0.0416(4) | 0.9429(6) | 0.3390(8) | 0.085(3) |
| O(5) | 0.8185(5) | 0.0004(8) | 0.2629(9) | 0.106(3) |
| N(1) | 0.0111(4) | 0.7607(6) | 0.4752(7) | 0.052(2) |

TABLE 3-continued

| | Coordinates | | | |
|---|---|---|---|---|
| Atom | x | y | z | u (eq) |
| C(1) | 0.2895(5) | 0.7107(9) | 0.4632(9) | 0.048(3) |
| C(2) | 0.3330(5) | 0.7876(8) | 0.3826(8) | 0.048(3) |
| C(3) | 0.3004(5) | 0.7672(8) | 0.2296(8) | 0.046(3) |
| C(4) | 0.4173(5) | 0.7650(8) | 0.4148(8) | 0.052(3) |
| C(5) | 0.1635(5) | 0.6746(9) | 0.497(1) | 0.062(3) |
| C(6) | 0.1435(5) | 0.7488(9) | 0.6085(9) | 0.057(3) |
| C(7) | 0.0989(6) | 0.6415(8) | 0.378(1) | 0.059(3) |
| C(8) | 0.0382(5) | 0.7325(9) | 0.3439(9) | 0.056(3) |
| C(9) | 0.0761(6) | 0.840(1) | 0.315(1) | 0.064(3) |
| C(10) | 0.1014(6) | 0.8974(8) | 0.443(1) | 0.060(3) |
| C(11) | 0.0785(5) | 0.8286(8) | 0.5540(9) | 0.053(3) |
| C(12) | -0.0632(6) | 0.826(1) | 0.444(1) | 0.086(4) |
| C(13) | -0.0063(6) | 0.6595(9) | 0.554(1) | 0.062(3) |
| C(14) | 0.4747(4) | 0.8652(9) | 0.430(1) | 0.030(2) |
| C(15) | 0.2839(5) | 0.6644(9) | 0.1629(9) | 0.055(3) |
| C(16) | 0.528(2) | 0.818(2) | 0.445(2) | 0.22(1) |
| C(17) | 0.5445(5) | 0.702(2) | 0.441(1) | 0.144(6) |
| C(18) | 0.2552(6) | 0.684(1) | 0.019(1) | 0.079(4) |
| C(19) | 0.2507(6) | 0.792(1) | -0.016(1) | 0.080(4) |
| H(1) | -0.0767 | 0.8453 | 0.5286 | 0.102 |
| H(2) | -0.0572 | 0.8919 | 0.3949 | 0.102 |
| H(3) | -0.1021 | 0.7810 | 0.3906 | 0.102 |
| H(4) | -0.0210 | 0.6826 | 0.6359 | 0.073 |
| H(5) | -0.0463 | 0.6178 | 0.4982 | 0.073 |
| H(6) | 0.0377 | 0.6134 | 0.5781 | 0.073 |
| H(7) | 0.1300 | 0.7026 | 0.6770 | 0.069 |
| H(8) | 0.1873 | 0.7915 | 0.6490 | 0.069 |
| H(9) | 0.1190 | 0.6284 | 0.2985 | 0.069 |
| H(10) | 0.0762 | 0.5750 | 0.4016 | 0.069 |
| H(11) | 0.1873 | 0.6082 | 0.5393 | 0.073 |
| H(12) | -0.0025 | 0.7116 | 0.2699 | 0.066 |
| H(13) | 0.1084 | 0.8383 | 0.2506 | 0.075 |
| H(14) | 0.1498 | 0.9329 | 0.4626 | 0.071 |
| H(15) | 0.0658 | 0.8734 | 0.6250 | 0.063 |
| H(16) | 0.2906 | 0.5927 | 0.2065 | 0.065 |
| H(17) | 0.2406 | 0.6258 | -0.0469 | 0.094 |
| H(18) | 0.2328 | 0.8191 | -0.1075 | 0.097 |
| H(19) | 0.4649 | 0.9443 | 0.4254 | 0.037 |
| H(20) | 0.5729 | 0.8656 | 0.4660 | 0.268 |
| H(21) | 0.5930 | 0.6651 | 0.4477 | 0.165 |
| H(22) | 0.8192 | -0.0610 | 0.1619 | 0.084 |
| H(23) | 0.7603 | 0.0105 | 0.2412 | 0.084 | x, y, z: fractional coordinates;
U(eq) mean quadratic amplitude of atomic movement in the crystal Characterisation of Crystalline, Anhydrous Tiotropium Bromide As described hereinbefore, the crystalline anhydrous tiotropium bromide according to the invention may be obtained from crystalline tiotropium bromide monohydrate. The crystalline structure of anhydrous tiotropium bromide was determined from high-resolution X-ray powder data (synchrotron radiation) using a real space approach with a so-called simulated annealing process. A final Rietveld analysis was carried out to refine the structural parameters. Table 4 contains the experimental data obtained for crystalline, anhydrous tiotropium bromide.

TABLE 4

Experimental data relating to the crystalline structural analysis of tiotropium bromide (anhydrous)

| | |
|---|---|
| formula | $C_{19}H_{22}NO_4S_2Br$ |
| temperature [° C.] | 25 |
| molecular weight [g/mol] | 472.4 |
| space group | P2$_1$/c |
| a [Å] | 10.4336(2) |
| b [Å] | 11.3297(3) |
| c [Å] | 17.6332(4) |

TABLE 4-continued

Experimental data relating to the crystalline structural analysis of tiotropium bromide (anhydrous)

| | |
|---|---|
| β [°] | 105.158(2) |
| V [Å$^3$] | 2011.89(8) |
| Z | 4 |
| calculated density [g cm$^{-3}$] | 1.56 |
| 2Θ (range) [°] | 2.0–20 |
| interval [°2Θ] | 0.003 |
| counting time/step [sec] | 3 |
| wavelength [Å] | 0.7000 |

Accordingly, the present invention relates to crystalline anhydrous tiotropium bromide, which is characterised by the elementary cells α=10.4336(2) Å,
b=11.3297(3) Å,
c=17.6332(4) Å and
α=90°,
β=105.158(2)° and
γ=90° (cell volume=2011.89(8) Å$^3$).

The crystalline structure of the anhydrous form of tiotropium bromide can be described as a layered structure. The bromide ions are located between the layers of tiotropium.

In order to clarify the structure of crystalline anhydrous tiotropium bromide a high-resolution X-ray powder diagram was taken at ambient temperature at the National Synchrotron Source (Brookhaven National Laboratory, USA) at measuring station X3B1 (λ=0.700 Å). For this experiment a sample of crystalline tiotropium bromide monohydrate was placed in a quartz glass capillary 0.7 mm in diameter. The water was eliminated by heating to 80° C. in an oven under reduced pressure.

The structural resolution was obtained by a so-called simulated annealing process. The DASH program package produced by Cambridge Crystallographic Data Center (CCDC, Cambridge, United Kingdom) was used for this.

Table 5 shows the atomic coordinates obtained for crystalline anhydrous tiotropium bromide.

TABLE 5

| Atom | Coordinates | | | |
|---|---|---|---|---|
| | x | y | z | U$_{iso}$ |
| S1 | 1.0951(8) | 0.3648(8) | 0.8189(5) | 0.075(9) |
| S1 | 0.9143(9) | 0.1374(8) | 0.9856(5) | 0.075(9) |
| O | 0.6852(13) | 0.2339(6) | 0.7369(6) | 0.075(9) |
| O1 | 0.7389(15) | 0.0898(9) | 0.8234(6) | 0.075(9) |
| O2 | 0.8211(10) | 0.3897(17) | 0.8277(7) | 0.075(9) |
| O3 | 0.4975(17) | 0.4816(9) | 0.6011(7) | 0.075(9) |
| N | 0.4025(10) | 0.2781(8) | 0.5511(5) | 0.075(9) |
| C | 0.7509(8) | 0.1885(6) | 0.8038(5) | 0.075(9) |
| C1 | 0.8593(7) | 0.2788(5) | 0.8495(4) | 0.075(9) |
| C2 | 0.9924(9) | 0.2533(6) | 0.8225(6) | 0.075(9) |
| C3 | 0.8884(9) | 0.2664(7) | 0.9382(4) | 0.075(9) |
| C4 | 0.5848(12) | 0.1596(8) | 0.6753(8) | 0.075(9) |
| C5 | 0.4544(13) | 0.1929(14) | 0.6809(8) | 0.075(9) |
| C6 | 0.6156(13) | 0.1810(13) | 0.5973(9) | 0.075(9) |
| C7 | 0.5493(11) | 0.2881(11) | 0.5578(6) | 0.075(9) |
| C8 | 0.5869(12) | 0.3832(11) | 0.6092(7) | 0.075(9) |
| C9 | 0.4947(13) | 0.3902(10) | 0.6575(6) | 0.075(9) |
| C10 | 0.4004(10) | 0.2998(11) | 0.6332(6) | 0.075(9) |
| C11 | 0.3220(13) | 0.3670(13) | 0.4935(6) | 0.075(9) |
| C12 | 0.3450(19) | 0.1643(26) | 0.5211(11) | 0.075(9) |
| C13 | 0.9184(16) | 0.3808(9) | 0.9920(6) | 0.075(9) |
| C14 | 1.0313(16) | 0.1552(15) | 0.8011(15) | 0.075(9) |
| C15 | 0.9515(17) | 0.3374(10) | 0.0501(6) | 0.075(9) |

TABLE 5-continued

| Atom | Coordinates | | | |
|---|---|---|---|---|
| | x | y | z | U$_{iso}$ |
| C16 | 0.9756(18) | 0.2190(11) | 1.0742(5) | 0.075(9) |
| C17 | 1.1483(22) | 0.1762(18) | 0.7718(24) | 0.075(9) |
| C18 | 1.1860(16) | 0.2800(15) | 0.7768(19) | 0.075(9) |
| BR | 0.4597(4) | 0.8200(15) | 0.61902(25) | 0.042(9) |

In the above Table the "U$_{iso}$" values denote the isotropic temperature factors. For example, in single-crystal X-ray structural analysis this corresponds to the u(eq) values.

Table 6 shows the reflexes (h,k,l indices) of the powder diagram obtained for crystalline ahydrous tiotropium bromide.

TABLE 6

Experimental data relating to the crystalline structural analysis of anhydrous tiotropium bromide

| No. | h | k | l | 2Θ$_{obs.}$ | 2Θ$_{calc.}$ | 2Θ$_{obs.}$ − 2Θ$_{calc}$ |
|---|---|---|---|---|---|---|
| 1 | 1 | 0 | 0 | 8.762 | 8.769 | −0.007 |
| 2 | 0 | 1 | 1 | 9.368 | 9.369 | −0.001 |
| 3 | −1 | 0 | 2 | 11.730 | 11.725 | 0.005 |
| 4 | 0 | 1 | 2 | 12.997 | 13.004 | −0.007 |
| 5 | −1 | 1 | 2 | 14.085 | 14.094 | −0.009 |
| 6 | 1 | 0 | 2 | 15.271 | 15.275 | −0.004 |
| 7 | 0 | 0 | 3 | 15.620 | 15.616 | 0.004 |
| 8 | 0 | 2 | 1 | 16.475 | 16.475 | 0.0 |
| 9 | 1 | 1 | 2 | 17.165 | 17.170 | −0.005 |
| 10 | 2 | 0 | 0 | 17.588 | 17.591 | −0.003 |
| 11 | −1 | 2 | 1 | 18.009 | 18.035 | −0.026 |
| 12 | 1 | 2 | 1 | 19.336 | 19.328 | 0.008 |
| 13 | −2 | 1 | 2 | 19.596 | 19.600 | −0.004 |
| 14 | −1 | 0 | 4 | 20.417 | 20.422 | −0.005 |
| 15 | 0 | 0 | 4 | 20.865 | 20.872 | −0.007 |
| 16 | 2 | 1 | 1 | 21.150 | 21.145 | 0.005 |
| 17 | −2 | 1 | 3 | 21.759 | 21.754 | 0.005 |
| 18 | 0 | 2 | 3 | 22.167 | 22.160 | 0.007 |
| 19 | −1 | 2 | 3 | 22.289 | 22.288 | 0.001 |
| 20 | 2 | 0 | 2 | 22.735 | 22.724 | 0.011 |
| 21 | −2 | 2 | 1 | 23.163 | 23.159 | 0.004 |
| 22 | −2 | 0 | 4 | 23.567 | 23.575 | −0.008 |
| 23 | 2 | 1 | 2 | 24.081 | 24.058 | 0.023 |
| 24 | 1 | 0 | 4 | 24.746 | 24.739 | 0.007 |
| 25 | −1 | 3 | 1 | 25.220 | 25.221 | −0.001 |
| 26 | 1 | 2 | 3 | 25.359 | 25.365 | −0.006 |
| 27 | 0 | 3 | 2 | 25.790 | 25.783 | 0.007 |
| 28 | 1 | 1 | 4 | 25.978 | 25.975 | 0.003 |
| 29 | 0 | 2 | 4 | 26.183 | 26.179 | 0.004 |
| 30 | −1 | 3 | 2 | 26.383 | 26.365 | 0.018 |
| 31 | −1 | 1 | 5 | 26.555 | 26.541 | 0.014 |
| 32 | −3 | 1 | 2 | 27.024 | 27.021 | 0.003 |
| 33 | 3 | 1 | 0 | 27.688 | 27.680 | 0.008 |
| 34 | −3 | 1 | 3 | 28.221 | 28.215 | 0.006 |
| 35 | 3 | 0 | 1 | 28.377 | 28.376 | 0.001 |
| 36 | −3 | 0 | 4 | 29.246 | 29.243 | 0.003 |
| 37 | 3 | 1 | 1 | 29.459 | 29.471 | −0.012 |
| 38 | −1 | 2 | 5 | 29.906 | 29.900 | 0.006 |
| 39 | −3 | 2 | 1 | 30.171 | 30.165 | 0.006 |
| 40 | 0 | 2 | 5 | 30.626 | 30.626 | 0.0 |
| 41 | 1 | 1 | 5 | 30.871 | 30.856 | 0.015 |
| 42 | 0 | 0 | 6 | 31.504 | 31.532 | −0.028 |
| 43 | 2 | 1 | 4 | 31.826 | 31.847 | −0.021 |
| 44 | −2 | 1 | 6 | 32.888 | 32.888 | 0.0 |
| 45 | 1 | 4 | 1 | 33.605 | 33.615 | −0.010 |
| 46 | 3 | 0 | 3 | 34.379 | 34.377 | 0.002 |
| 47 | 1 | 0 | 6 | 35.021 | 35.018 | 0.003 |
| 48 | −4 | 1 | 1 | 35.513 | 35.503 | 0.01 |
| 49 | 1 | 1 | 6 | 35.934 | 35.930 | 0.004 |
| 50 | −1 | 1 | 7 | 36.544 | 36.543 | 0.001 |
| 51 | −4 | 1 | 4 | 37.257 | 37.255 | 0.002 |
| 52 | −4 | 2 | 2 | 37.933 | 37.952 | −0.019 |
| 53 | 4 | 1 | 1 | 38.258 | 38.264 | −0.006 |

According to another aspect, the present invention relates to the use of crystalline anhydrous tiotropium bromide as a medicament in the light of the pharmaceutical efficacy of the anhydrous form according to the invention. To prepare a medicament which can be inhaled, particularly an inhalable powder, which contains the anhydrous, crystalline tiotropium bromide described by the present invention, methods known from the prior art may be used. In this respect, reference is made, for example, to the teaching of DE-A-179 22 07. Accordingly a further aspect of the present invention relates to inhalable powders characterised in that they contain anhydrous, crystalline tiotropium bromide.

Because of the potency of tiotropium bromide, the powders for inhalation mentioned above preferably contain, in addition to the active substance, the following physiologically acceptable excipients. The following physiologically acceptable excipients may be used, for example: monosaccharides (e.g. glucose or arabinose), disaccharides (e.g. lactose, sucrose, maltose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients which are characterised in that they contain anhydrous crystalline tiotropium bromide have a maximum average particle size of up to 250 μm, preferably between 10 and 150 μm, most preferably between 15 and 80 μm. It may sometimes seem appropriate to add finer excipient fractions with an average particle size of 1 to 9 μm to the excipients mentioned above. These finer excipients are also selected from the group of possible excipients listed hereinbefore.

Preferred inhalable powders containing the tiotropium bromide anhydrate according to the invention are characterised in that the excipient consists of a mixture of coarser excipient with an average particle size of from 17 to 50 μm, more preferably 20 to 30 μm, and finer excipient with an average particle size of 2 to 8 μm, more preferably 3 to 7 μm. The term average particle size here denotes the 50% value from the volume distribution measured with a laser diffractometer by the dry dispersion method. Inhalable powders wherein the proportion of finer excipient in the total quantity of excipient is 3 to 15%, more preferably 5 to 10%, are preferred.

One possible method of preparing these inhalable powders which are preferred according to the invention is discussed in more detail hereinafter.

After the starting materials have been weighed out, first the excipient mixture is prepared from the defined fractions of the coarser excipient and finer excipient. Then the inhalable powders according to the invention are prepared from the excipient mixture and the active substance. If the inhalable powder is to be administered by means of inhalettes in suitable inhalers, the preparation of the inhalable powders is followed by the production of the capsules containing the powder.

The inhalable powders according to the invention are prepared by mixing the coarser excipient fractions with the finer excipient fractions and subsequently mixing the resulting excipient mixtures with the active substance.

In order to prepare the excipient mixture the coarser and finer excipient fractions are placed in a suitable mixing container. The two components are preferably added through a screening granulator with a mesh size of 0.1 to 2 mm, most preferably 0.3 to 1 mm, even more preferably 0.3 to 0.6 mm. Preferably the coarser excipient is put in first and then the finer excipient fraction is added to the mixing container. In this mixing process the two components are preferably added batchwise, with half the coarser excipient being put in first followed by finer and coarser excipient added alternately. It is particularly preferable when preparing the excipient mixture to screen the two components in alternate layers. Preferably this screening of the two components takes place in 15 to 45, more preferably in 20 to 40 alternate layers. The mixing of the two excipients may take place while the two components are being added. However, it is preferably not done until the layers of ingredients have been added.

After the preparation of the excipient mixture, this and the active substance are placed in a suitable mixing container. The active substance used has an average particle size of 0.5 to 10 μm, preferably 1 to 6 μm, more preferably 2 to 5 μm. The two components are preferably added through a screening granulator with a mesh size of 0.1 to 2 mm, most preferably 0.3 to 1 mm, even more preferably 0.3 to 0.6 mm. Preferably the excipient mixture is put in first and then the active substance is added to the mixing container. It is particularly preferable when preparing the excipient mixture to screen the two components in alternate layers. Preferably this screening of the two components takes place in 25 to 65, more preferably in 30 to 60 alternate layers. The mixing of the excipient mixture with the active substance may take place while the two components are being added. However, it is preferably not done until the layers of ingredients have been added.

The powder mixture thus obtained may optionally be passed through a screening granulator once again or several times more and then subjected to another mixing operation each time.

The inhalable powders obtained by the above method preferably contain about 0.001 to 2% tiotropium bromide in admixture with a physiologically acceptable excipient. Preferred are inhalable powders which contain 0.04 to 0.8% of tiotropium bromide in admixture with a physiologically acceptable excipient, characterised in that the excipient consists of a mixture of coarser excipient with an average particle size of 15 to 80 μm and finer excipient with an average particle size of 1 to 9 μm, the proportion of finer excipient in the total quantity of excipient being 1 to 20%. According to the invention, inhalable powders which contain 0.08 to 0.64%, more preferably 0.16 to 0.4% tiotropium bromide, are preferred.

If anhydrous crystalline tiotropium bromide is included in the inhalable powders mentioned above, these powder mixtures preferably contain 0.0012–2.41% of tiotropium bromide anhydrate. Also preferred are inhalable powders which contain between 0.048 and 0.96% of tiotropium bromide anhydrate. Of particular interest according to the invention are inhalable powders which contain 0.096 to 0.77%, more preferably 0.19 to 0.48% tiotropium bromide anhydrate.

The percentages mentioned within the scope of the present invention are always percent by weight.

An alternative, equally preferred embodiment for preparing inhalable powders containing tiotropium bromide anhydrate may also be prepared from inhalable powders formulated on the basis of the crystalline tiotropium bromide monohydrate. These contain between 0.0012 and 2.5%, preferably 0.05 to 1%, preferably 0.1 to 0.8%, more preferably 0.2 to 0.5% crystalline tiotropium bromide monohydrate and may preferably be obtained analogously to the process described hereinbefore. These inhalable powders containing crystalline tiotropium bromide monohydrate may be dried in order to prepare inhalable powders containing the tiotropium bromide anhydrate according to the invention, either before being packed into the inhalation capsules or, preferably, after being packed into the corresponding inhalation capsules, at more than 60° C., preferably at 65–100° C., more preferably at 70–100° C., under reduced pressure, preferably under a high vacuum, over a period of 15 minutes to 24 hours, preferably 20 minutes to 12 hours, more preferably 30 minutes to 6 hours. The term reduced pressure particularly denotes a pressure of up to $5\times10^{-2}$ bar, preferably $1\times10^{-2}$ bar, more preferably $5\times10^{-3}$ bar.

Most preferably, the dehydration mentioned above to form the anhydrate is carried out at about $1\times10^{-3}$ bar or less.

In view of the anticholinergic effects of tiotropium bromide a further aspect of the present invention relates to the use of crystalline anhydrous tiotropium bromide for preparing a pharmaceutical composition for treating diseases in which the use of an anticholinergic agent may have a therapeutic benefit. It is preferably used for preparing a pharmaceutical composition for treating asthma or COPD.

The following example of synthesis serves to illustrate a method of preparing anhydrous crystalline tiotropium bromide carried out by way of example. It is to be regarded only as a possible method described by way of example, without restricting the invention to its contents.

EXAMPLE OF SYNTHESIS

A) Preparation of Crystalline Tiotropium Bromide Monohydrate:

In a suitable reaction vessel 15.0 kg of tiotropium bromide are added to 25.7 kg of water. The mixture is heated to 80–90° C. and stirred at constant temperature until a clear solution is formed. Activated charcoal (0.8 kg), moistened with water, is suspended in 4.4 kg of water, this mixture is added to the solution containing the tiotropium bromide and rinsed with 4.3 kg of water. The mixture thus obtained is stirred for at least 15 min at 80–90° C. and then filtered through a heated filter into an apparatus which has been preheated to an outer temperature of 70° C. The filter is rinsed with 8.6 kg of water. The contents of the apparatus are cooled to a temperature of 20–25° C. at a rate of 3–5° C. per 20 minutes. The apparatus is further cooled to 10–15° C. using cold water, and the crystallisation is completed by stirring for at least one hour. The crystals are isolated using a suction filter drier, the crystal slurry isolated is washed with 9 l of cold water (10–15° C.) and cold acetone (10–15° C.). The crystals obtained are dried at 25° C. for 2 hours in a nitrogen current.
Yield: 13.4 kg of tiotropium bromide monohydrate (86% of theory)

B) Preparation of Crystalline Anhydrous Tiotropium Bromide:

The anhydrous form is produced from the crystalline tiotropium bromide monohydrate obtained as described above by careful drying at 80–100° C. under reduced pressure, preferably under a high vacuum (at about $1\times10^{-3}$ bar or less) over a period of at least 30 minutes. Alternatively to the drying step at 80–100° C. in vacuo the anhydrous form may also be prepared by storing over dried silica gel at ambient temperature for a period of at least 24 hours.

What is claimed is:

1. Anhydrous cyrstalline tiotropium bromide.

2. Anhydrous crystalline tiotropium bromide according to claim 1, having a monoclinic crystal system wherein a monoclinic elementary cell has the parameters a=10.4336(2) Å, b=11.3297(3) Å, c=17.6332(4) Å, α=90°, β=105.158(2)° and γ=90° (cell volume=2011.89(8) Å$^3$) as determined by X-ray structural analysis.

3. A process for preparing crystalline, anhydrous tiotropium bromide which comprises (a) dissolving tiotropium bromide in water;
    (b) heating the resulting solution;
    (c) crystallizing the hydrate of tiotropium bromide while cooling slowly; and
    (d) drying the resulting crystalline tiotropium bromide monohydrate.

4. The process according to claim 3, wherein drying is at about 60° C. to about 100° C.

5. The process according to claim 3, wherein drying is carried out over a period of from about 15 minutes to about 24 hours.

6. A process for preparing crystalline, anhydrous tiotropium bromide, according to claim 3, wherein drying is accomplished by storing crystalline tiotropium bromide monohydrate over a suitable drying agent for a period of about 12 to about 96 hours.

7. Crystalline anhydrous tiotropium bromide obtained by the process of claim 3.

8. Crystalline anhydrous tiotropium bromide obtained by the process of claim 4.

9. Crystalline anhydrous tiotropium bromide obtained by the process of claim 5.

10. Crystalline anhydrous tiotropium bromide obtained by the process of claim 6.

11. A pharmaceutical composition of matter comprising crystalline anhydrous tiotropium bromide as recited in claim 2.

12. The pharmaceutical composition of matter according to claim 11, which is an inhalable powder.

13. A pharmaceutical composition of matter comprising crystalline anhydrous tiotropium bromide as recited in claim 7.

14. The pharmaceutical composition of matter as recited in claim 13, which is an inhalable powder.

15. A pharmaceutical composition of matter comprising crystalline anhydrous tiotropium bromide as recited in claim 9.

16. The pharmaceutical composition of matter according to claim 15, which is an inhalable powder.

17. A pharmaceutical composition of matter comprising crystalline anhydrous tiotropium bromide as recited in claim 10.

18. The pharmaceutical composition of matter according to claim 17, which is an inhalable powder.

* * * * *